(12) United States Patent
Lagesson et al.

(10) Patent No.: US 6,305,213 B1
(45) Date of Patent: Oct. 23, 2001

(54) DEVICE IN A GAS FLOW CELL AND A METHOD OF ANALYZING CHEMICAL SUBSTANCES BY MEANS OF THE GAS FLOW CELL

(76) Inventors: Verner Lagesson; Ludmila Lagesson-Andrasko, both of Kobergsgrand 2, S-587 21 Linkoping (SE)

( * ) Notice: Subject to any disclaimer, the term of this patent is extended or adjusted under 35 U.S.C. 154(b) by 0 days.

(21) Appl. No.: 09/526,771

(22) Filed: Mar. 16, 2000

Related U.S. Application Data

(63) Continuation of application No. PCT/SE98/01589, filed on Sep. 8, 1998.

(30) Foreign Application Priority Data

Sep. 26, 1997 (SE) .................................................. 9703477

(51) Int. Cl.[7] .................................................. G01N 601/10
(52) U.S. Cl. ........................ 73/23.39; 356/246; 356/437
(58) Field of Search .................................. 356/437, 242, 356/244; 73/23.37, 23.39

(56) References Cited

U.S. PATENT DOCUMENTS

| | | | |
|---|---|---|---|
| 2,972,246 | * 2/1961 | Reinecke et al. | 73/23.39 |
| 3,869,214 | * 3/1975 | Egli et al. | 356/246 |
| 4,440,013 | 4/1984 | Adams | 73/23.37 |
| 4,588,893 | * 5/1986 | Vidrine et al. | 356/246 |
| 4,668,091 | 5/1987 | Lagesson et al. | 356/246 |

FOREIGN PATENT DOCUMENTS

| | | | |
|---|---|---|---|
| 0187 306 | 7/1986 | (EP) . | |
| 56087843-A | * 7/1981 | (JP) | 356/244 |

OTHER PUBLICATIONS

International Search Report for PCT/SE98/01589.

* cited by examiner

*Primary Examiner*—Hezron Williams
*Assistant Examiner*—Michael Cygan
(74) *Attorney, Agent, or Firm*—Altera Law Group, LLC

(57) ABSTRACT

The present invention relates to a device in gas flow cells for the analysis of chemical substances by spectrophotometry. The gas flow cell has two longitudinal ducts, which are connected by a connection so that a first flow is permitted though the ducts and the connection. The first duct in the direction of flow has a separation column and the second duct is a light guide. The invention is characterized in that in the connection there is a coupling, which is connected with the outlet from an external separation unit. The connection is designed to receive a second flow comprising the substances separated in the external separation unit together with a first carrier gas, so that the second flow is added to the first flow in the connection. The device is designed to function in either of two operating positions, where in the first position the device functions in the conventional manner and where in the second position the first flow comprises the second carrier gas and the second flow is connected up. The invention also relates to a method of analyzing chemical substances.

4 Claims, 4 Drawing Sheets

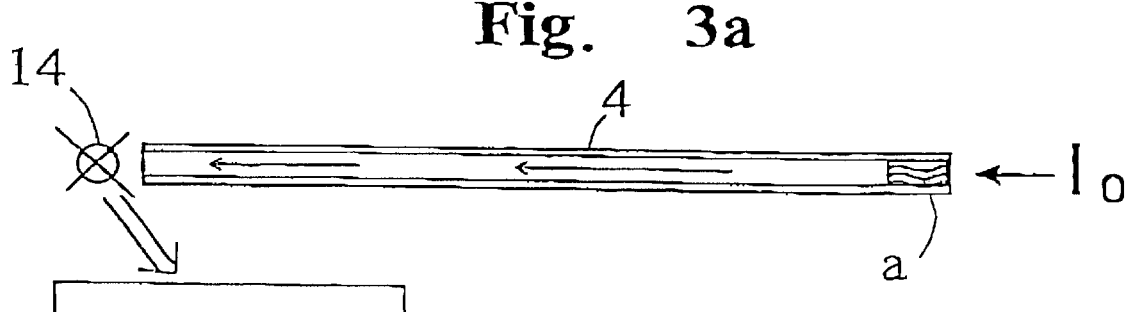
Fig. 3a
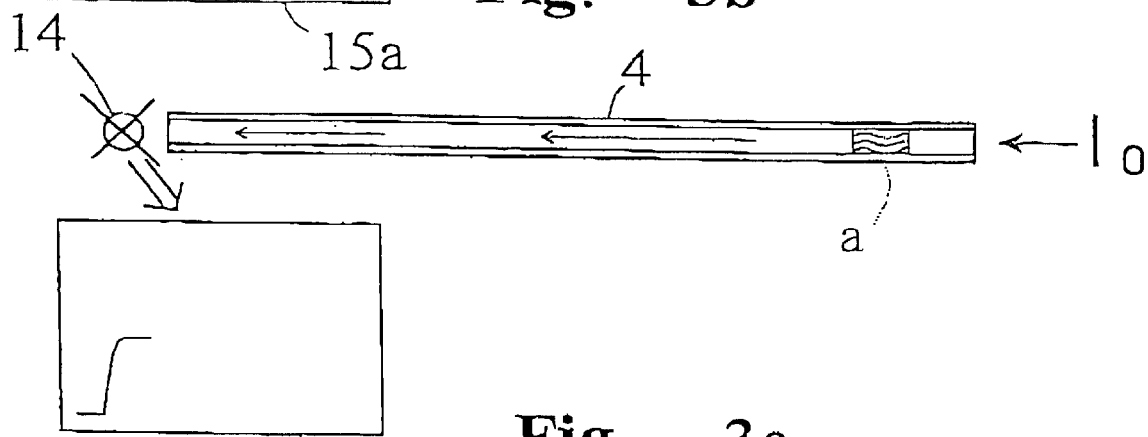
Fig. 3b
Fig. 3c
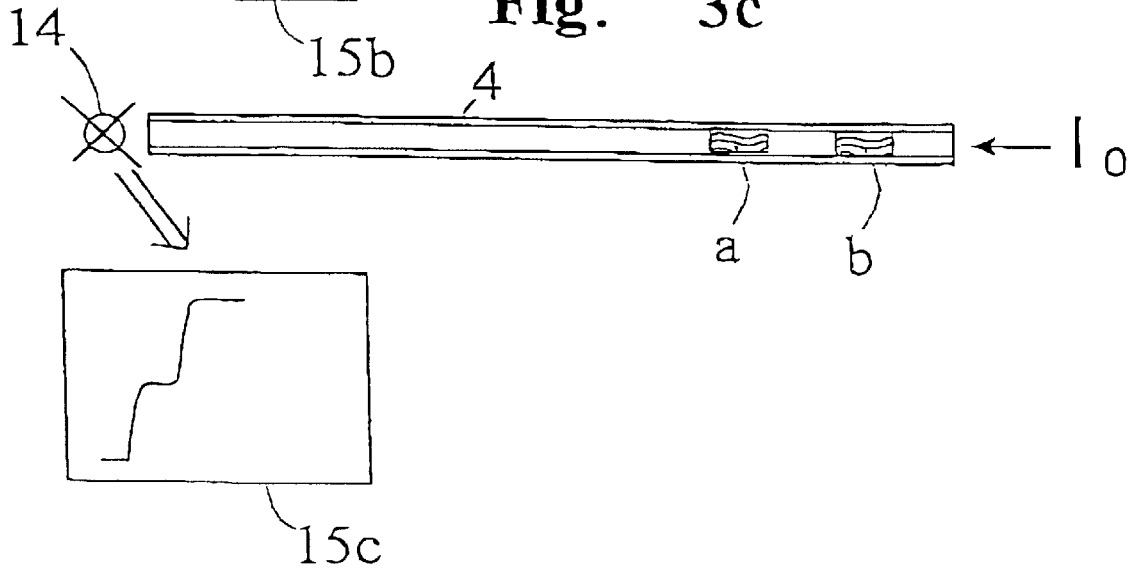

DEVICE IN A GAS FLOW CELL AND A METHOD OF ANALYZING CHEMICAL SUBSTANCES BY MEANS OF THE GAS FLOW CELL

This is a continuation of PCT/SE98/01589 filed Sep. 8, 1998.

FIELD OF THE INVENTION

The present invention relates to a device in a gas flow cell for the analysis of chemical substances by means of spectrophotometry.

The present invention also relates to a method of analyzing chemical substances.

DESCRIPTION OF RELATED ART

That part of analytical chemistry dealing with the separation and detection of mixtures of organic substances has been dominated since the nineteen-sixties by gas chromatography. In recent years development has tended towards combining gas chromatography (GC) with some qualitative method of analysis such as mass spectroscopy (MS), IR spectrophotometry (IR) or UV spectrophotometry (UV). The advantage with these combinations resides primarily in the fact that they make it possible to identify the substances separated by means of the gas chromatograph. Furthermore, detection/ identification can be rendered specific by having the detector give a reading for certain groups of substances, for example aldehydes.

U.S. Pat. No. 4,668,091 shows a gas flow cell for the analysis of chemical substances by spectrophotometry. The gas flow cell has an elongated, cylindrical body. It comprises two longitudinal ducts, connected to one another by a passage. One of the ducts comprises a separation column and at its first end has connections for the introduction of a carrier gas and for injection of the substances. The carrier gas and the substances form a flow through the separation column duct and leave this at its second end. The second duct is a light guide duct, which the flow from the separation column duct enters via the passage at a first end and leaves through an outlet at the second end of the light duct. Furthermore two gas-tight windows are arranged essentially parallel to one another at respective ends of the light duct, the windows being transparent for radiation used in the analysis.

The above-mentioned device according to the prior art is characterised by short analysis times, a good capability for separating out specific constituents and a high test capacity.

SUMMARY OF THE INVENTION

According to one embodiment of the present invention, a device is created in a gas flow cell for the analysis of chemical substances by spectrophotometry.

According to another embodiment of the present invention a method is created for the analysis of chemical substances.

The device according to the invention in the gas flow cell according to the present invention has several advantages. One important advantage is that, in addition to having the features characteristic of gas flow cell devices according to the prior art, it also has a good capability for separating the constituents of complex compounds. Other advantages are the fact that the device is easy to handle and that the capability for separating the constituents of complex compounds can be obtained without converting instruments.

BRIEF DESCRIPTION OF THE DRAWINGS

The invention will be described in more detail below with reference to the drawing, which shows an example of an embodiment of the invention.

FIGS. 3a, 3b and 3c show the flow through the light guide duct in the gas flow cell according to FIG. 1 at various stages when only the external flow is connected up.

DETAILED DESCRIPTION

Figure 1:
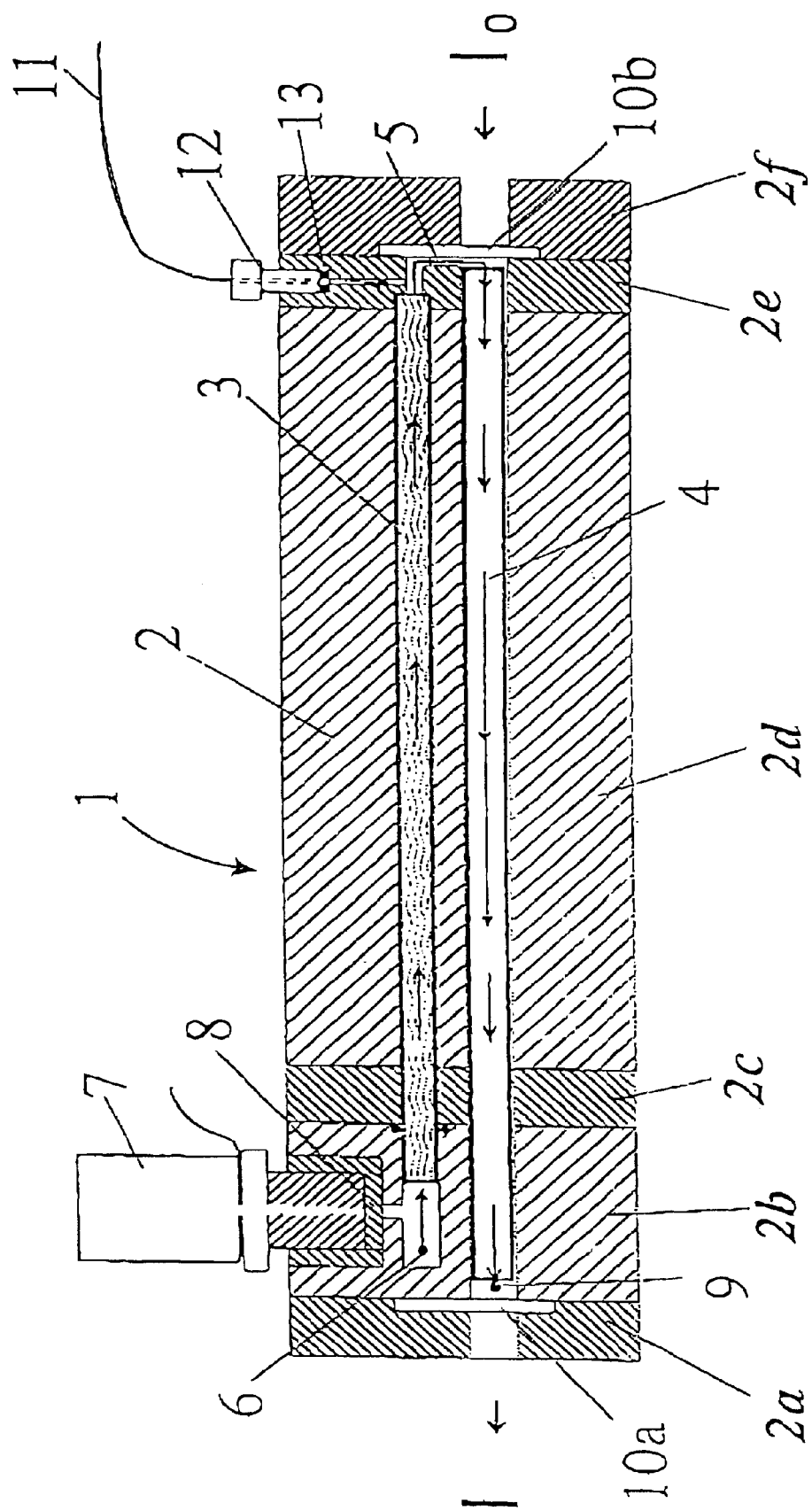
FIG. 1 shows a gas flow cell according to the present invention, for the analysis of chemical substances by spectrophotometry.

In FIG. 1, the reference number 1 generally denotes a gas flow cell for the analysis of chemical substances by spectrophotometry. The gas flow cell 1 is made at least partially of a carbon-filled polymer material, which withstands high temperatures and which is electrically conductive, it being possible to control the temperature of the cell 1 by feeding a variable electrical current through the actual material of which it is made.

The gas flow cell 1 has an elongated, cylindrical body 2. It is preferably dimensioned so that it fits into the dish housing (not shown) of the spectrophotometer. In this example the spectrophotometer is a UV spectrophotometer.

The body 2 comprises two longitudinal ducts 3, 4, which are connected to one another by a connection 5, essentially located radially in the cylinder 2. One of the ducts 3 comprises a separation column 3 and at its first end has a connection 6 for the introduction of a carrier gas. Also arranged at the same end is an injector 7, designed to selectively inject the chemical substances to be analysed into the duct 3 via an injector diaphragm 8.

The carrier gas and the substances, where present, thus form an internal flow through the duct 3 for the separation column, the flow leaving the latter at it second end. The second duct is a duct 4 for a light guide, which the flow from the duct 3 enters via the connection 5 at a first end and leaves through an outlet 9 at the second end of the light guide duct 4. The arrows shown in the ducts 3, 4 and the connection 5 in FIG. 1 indicate the direction of flow in the gas flow cell 1. Two gas-tight windows 10a, 10b, for example quartz windows, are arranged essentially parallel to one another at respective ends of the light duct, the windows being transparent for radiation used in the analysis. The incoming radiation, for example ultraviolet light, is denoted in the figure by $L_O$ and, as indicated by an arrows enters the light guide duct 4 via the window 10b at the same end as the flow. The outgoing radiation is denoted by I and leaves the cylinder body 2 via the window 10a for analysis by means of a detector, which will be described later.

The cylindrical body is made in six parts 2a, 2b, 2c, 2d, 2e and 2f, joined together by screws and, where necessary, mutually sealed by means of O-rings.

The outlet from an external gas chromatography separation unit (not shown) communicates selectively with the connection 5 via a communicating duct 11 through a coupling in that connection 5. The external gas chromatography separation unit differs from the separation column in the duct 3 in that it has a very good capability for separating the constituents of complex compounds. The coupling of the communicating duct 11 to the connection 5 is made in part 2e of the body 2. The passage in part 2e is made via a bored screw 12 and a seal 13, for example an O-ring seal 13, through which the communicating duct 11 enters the body 2.

When the chemical substances are separated in the external separation unit an external flow is formed comprising the separated substances and carrier gas. This external flow enters the connection 5 via the communicating duct 11, continuing thence to the light guide duct 4 in the same way as the internal flow. The external flow is thus added through the communicating duct 11 to the internal flow through the duct 3 for the separation column, the light guide duct 4 receiving a total flow which derives partly from the internal flow from the duct 3 for the separation column and partly from the external flow from the communicating duct 11. By adding the internal flow to the external flow in this way, an increase in the rate of flow through the light guide duct is achieved.

The device according to the invention can also work in two positions. In the first position, which is used, for example, to separate out specific constituents of a substance, a specimen is analysed in the conventional way by means of the gas flow cell separation technique, the carrier gas entering the gas flow cell via the connection 6 and the chemical substances being injected through the injector 7, with no external flow passing through the communicating duct 11. In the second position, which is used, for example, for separating out the constituents of complex compounds, the external separation unit is utilised, the external flow described above entering the gas flow cell 1 via the communicating duct 11 in the manner described above. Since sharp separations are required for dividing up the constituents, the "dead volume" of the light guide duct must be filled up in this position. This is done, after calculating what additional gas flow is required, by feeding the calculated additional flow through the coupling 6 to the duct 3 for the separation column in the form of the internal flow. How such a calculation must be performed will be obvious to the person skilled in the art and will be described in more detail in connection with an example described below. It must be emphasised that in this position no substances are injected through the injector 7. By adding an additional flow in this way the resolution is considerably improved, that is to say the device can separate adjacent peas. These alternative techniques can be selected without any conversion of instruments.

An example of a process in a gas flow cell according to the present invention is described below. The example relates to a situation in which two substances are separated externally by means of capillary gas chromatography and coupled to the present gas flow cell through the communicating duct 11. In a characteristic case the separation time may be in the order of approximately 10 minutes. The peaks corresponding to the substances to be detected when the flow passes through the light guide duct characteristically lie within 3 seconds, and the rate of flow of the external flow through the communicating duct 11 from the external separation unit is characteristically 1 cm$^3$/min.

Figure 2:
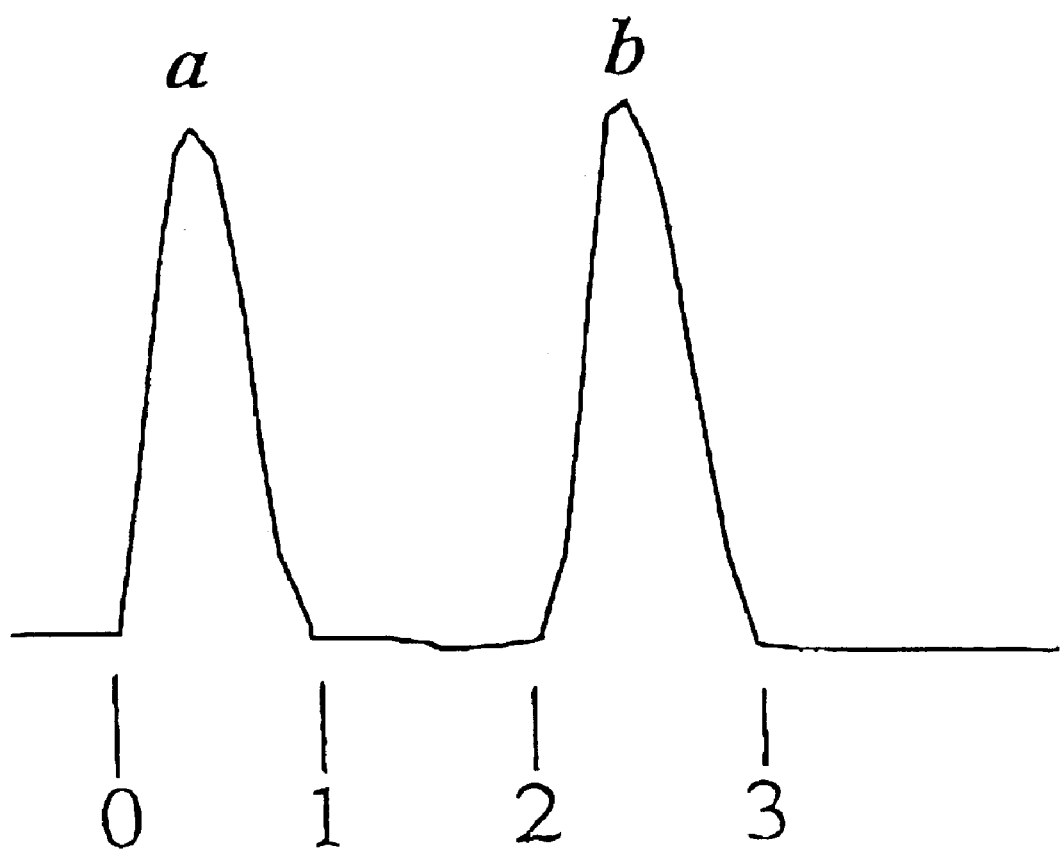
FIG. 2 shows an external substance flow to the gas flow cell according to FIG. 1.

FIG. 2 illustrates how the substance peaks in this external flow may be located in relation to one another, where the figures indicate the time in seconds and where a indicates the first substance and b indicates the second substance. As will be seen from FIG. 2, the peak for substance a is visible for one second, following which no substance is visible for one second and finally the peak for substance b is visible for one second. Factors such as diffusion and turbulence may cause a certain broadening of the peaks, but do not affect the basic principle and have not been incorporated in the example.

The example will be compared with a case in which no additional flow (through the internal flow) is applied via the connection 6 and the duct 3 for the separation column, only the external flow passing through the light guide duct 4. This case is shown in FIGS. 3a, 3b and 3c, in which the reference number 14 indicates a detector, the signal from which is shown as a function of time in boxes 15a, 15b and 15c associated with the detector in each figure respectively. The external flow is typically 1 cm$^3$/min, as stated previously, whilst the volume of the light guide duct is typically about 200 mm$^3$. This gives a through-flow time for the external flow of 200 mm$^3 \div 1$ cm$^3$/min=12s. When the first substance a is introduced via the flow into the light guide duct, the detector signal rises, as shown in the box 15a in FIG. 3a, and then after one second remains at a first level, as can be seen in box 15b in FIG. 3b, when the full peak has entered the light guide. The detector detects this first level until substance b enters the light guide duct 4, whereupon the detector again detects a rise until the full peak for substance b has entered the light guide duct, the detector signal approaching a second level. This can be seen in box 15c in FIG. 3c. The second level remains for 9s, following which the detector detects that the level is falling, since substance a is then leaving the light guide duct. The detector signals for substances a and b are therefore mixed for a large proportion of the detection time, it being difficult to resolve the different peaks. If more than two substances are to be separated, it naturally becomes even more difficult to resolve the peaks of the incoming substances.

Figure 4A:
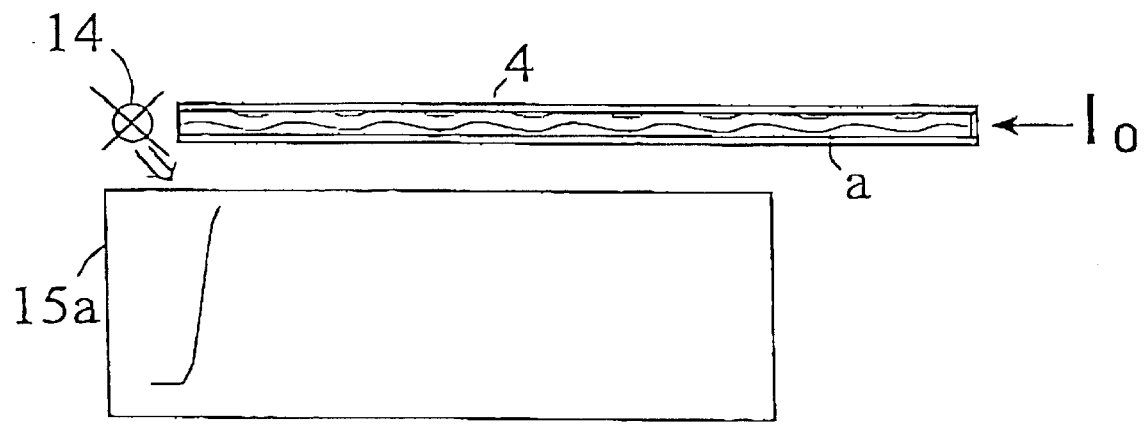
FIGS. 4a, 4b and 4c show the flow through the light guide duct in the gas flow cell according to FIG. 1 at various stages when both the external flow and an internal flow are connected up.
Figure 4B:
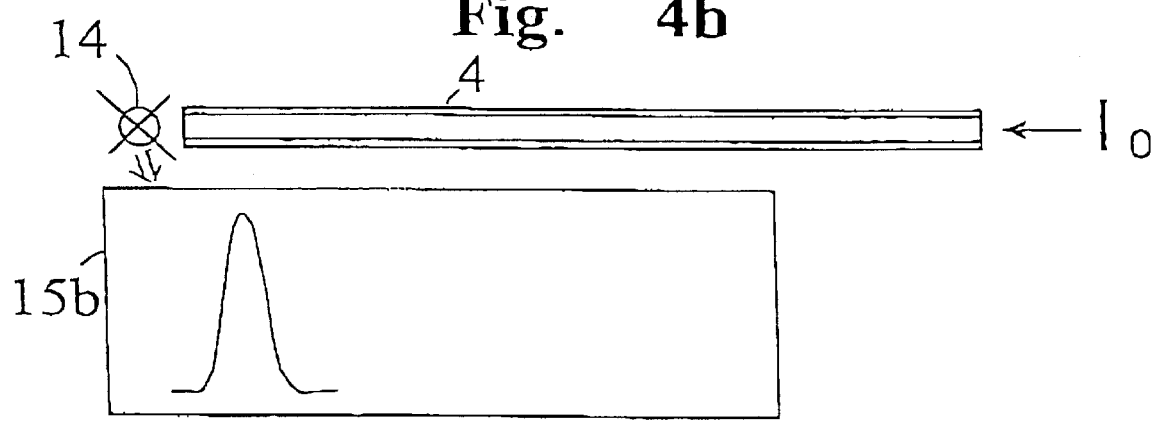
Figure 4C:
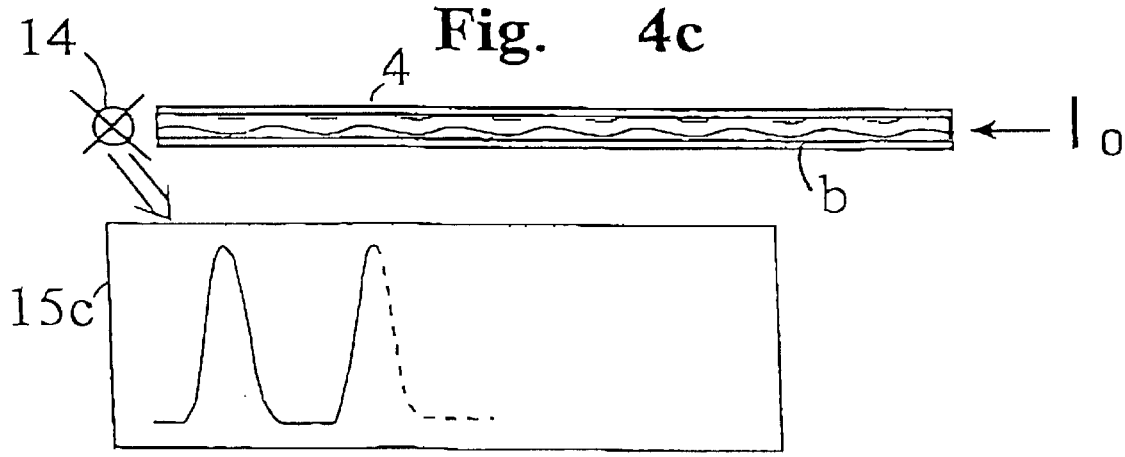

In the case shown in the example, the external flow is still 1 cm$^3$/min, whilst the internal flow consisting of carrier gas is 11 cm$^3$/min. Due to the addition of this internal flow, the rate of flow through the light carrier duct increases, the through-flow time being 200 m$^3 \div 12$ cm$^3$/min=1s. This case is shown in FIGS. 4a, 4b, 4c, in which reference number 14 again indicates a detector, the signal from which is shown as a function of time in the boxes 15a, 15b and 15c associated with the detector in each figure respectively. With this though-flow time the peak for the first substance a fills the entire light guide duct (the peak lasts for 1s and the flow time through the light guide duct is 1s), as can be seen in box 15a in FIG. 4a. For the next second the detector does not register any substance in the light guide duct, as can be seen in box 15b in FIG. 4b. Finally the second substance b is registered for 1s, as can be seen in box 15c in FIG. 4c. In this way pure spectra are obtained for substance a and substance b respectively.

Naturally this is merely an example by way of illustration and, as previously mentioned, the advantages of the present invention will be even more clearly apparent if a larger number of substances are being separated for detection in the light guide duct 4. With regard to the internal flow, it should also be possible to select this so that substances a and b are both in the light guide duct for a shorter period, or so that the through-flow time through the light guide duct is shorter than the length of the peaks for substances a and b. In most applications, however, it is advantageous if the through-flow time is approximately equal to the width of the peaks.

What is claimed is:

1. Device in a gas flow cell (1) for the analysis of chemical substances by spectrophotometry, the gas flow cell (1) having an elongated, preferably cylindrical body (2), which comprises two longitudinal ducts (3,4), connected to one another by an essentially radial connection (5) so that a first flow is permitted through the ducts (3,4) and the connection (5), where the first duct (3) in the direction of flow has a separation column and the second duct (4) is a light guide duct, characterised in that in the connection (5) there is a coupling, which is connected via a communicating duct (11) with the outlet from an external separation unit, designed to separate the chemical substances, and which is designed to receive a second flow comprising the substances separated in the external separation unit together with a first carrier gas, so that the second flow is added to the first flow in the connection (5), the device being able to switch over to either of two operating positions, where in the first position the first flow comprises the chemical substances and a second carrier gas and the other flow is stopped, and where in the second position the first flow comprises the second carrier gas and the second flow is connected up.

2. Device according to claim 1, characterised in that the first flow in the second position is designed to increase the rate of flow through the light guide duct (4).

3. Device according to claim 1, charcterised in that the first carrier gas is the same as the second carrier gas.

4. Method of analyzing chemical substances, characterised in that a gas flow cell (1) is created for analysis of the chemical substances by spectrophotometry, the gas flow cell (1) having an elongated, preferably cylindrical body (2), which comprises two longitudinal ducts (3,4), which are connected to one another via an essentially radial connection (5) so that a first flow is permitted through the ducts (3,4) and the connection (5), where the first duct (3) in the direction of flow has a separation column and the second duct (4) is a light guide.

the gas flow cell (1) in the connection (5) is connected via a communicating duct (11) to the outlet from an external separation unit, designed to separate the chemical substances, so that it is possible at the connection (5) to receive a second flow from the communicating duct (11) comprising the substances separated in the external separation unit together with a first carrier gas, this flow being added to the first flow, and control is permitted so that either the first flow is made to contain the chemical substances and a second carrier gas, whilst the second flow is stopped, or the first flow is made to consist of the second carrier gas whilst the second flow is connected up.

* * * * *